United States Patent [19]

Steinberg et al.

[11] Patent Number: 4,618,440
[45] Date of Patent: Oct. 21, 1986

[54] SUBSTITUTED 4-HYDROXYBENZYLTHIO ALDEHYDE AND KETONE STABILIZERS

[75] Inventors: David H. Steinberg, New York; John J. Luzzi, Carmel; Frank P. Cortolano, Valhalla, all of N.Y.

[73] Assignee: Ciba-Geigy Corporation, Ardsley, N.Y.

[21] Appl. No.: 815,772

[22] Filed: Jan. 2, 1986

Related U.S. Application Data

[63] Continuation of Ser. No. 743,224, Jun. 10, 1985, abandoned, which is a continuation of Ser. No. 544,297, Oct. 21, 1983, abandoned.

[51] Int. Cl.⁴ .................. C07C 149/273; C08K 5/37
[52] U.S. Cl. .................. 252/48.2; 524/289; 524/330; 524/336; 568/41; 568/43
[58] Field of Search ............ 568/41, 43; 252/48.2; 524/330, 336, 289

[56] References Cited

U.S. PATENT DOCUMENTS

| | | | |
|---|---|---|---|
| 2,461,013 | 2/1949 | Howells ........................ | 568/41 |
| 3,247,240 | 4/1966 | Meier et al. ................... | 524/336 |
| 3,536,661 | 10/1970 | Hagemeyer et al. ......... | 524/330 |
| 3,553,163 | 1/1971 | Spacht ........................... | 524/330 |
| 3,553,270 | 1/1971 | Wollensak et al. ........... | 524/330 |
| 3,590,085 | 6/1971 | Braus et al. ................... | 524/330 |
| 3,624,143 | 11/1971 | Shen et al. ..................... | 260/516 |
| 3,743,623 | 7/1973 | Kleiner .......................... | 524/289 |
| 3,810,869 | 5/1974 | Zaweski et al. ............... | 524/289 |
| 3,903,173 | 9/1975 | Eggensperger et al. ...... | 260/609 F |
| 3,953,398 | 4/1976 | Kline ............................. | 524/291 |
| 4,340,695 | 7/1982 | Schubart et al. .............. | 525/350 |
| 4,394,476 | 7/1983 | Cottman ........................ | 524/289 |

OTHER PUBLICATIONS

CA 77 89193a (1972)—Takano et al.
CA 64 17565f (1966)—Frisell et al.
CA 77 102977f (1972)—Yamamoto et al.

Primary Examiner—Veronica P. Hoke
Attorney, Agent, or Firm—Luther A. R. Hall; Harry Falber

[57] ABSTRACT

The title compounds correspond to the formula

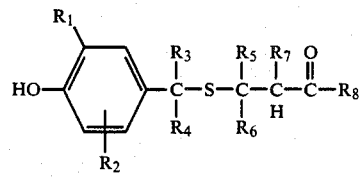

where $R_1$ is tert-butyl, $R_2$ is methyl or tert-butyl, $R_3$, $R_4$ and $R_7$ are hydrogen, $R_5$ and $R_8$ are hydrogen or methyl, and $R_6$ is hydrogen, alkyl of 1 to 3 carbon atoms or phenyl, and are useful as stabilizers for organic polymers and lubricating oils to counteract the degradative effects of heat, light and air.

10 Claims, No Drawings

SUBSTITUTED 4-HYDROXYBENZYLTHIO ALDEHYDE AND KETONE STABILIZERS

This is a continuation of application Ser. No. 743,224, filed on June 10, 1985, now abandoned, which in turn is a continuation of application Ser. No. 544,297, filed on Oct. 21, 1983, now abandoned.

Organic polymeric materials such as plastics and resins, and lubricating and mineral oils are subject to thermal, oxidative and photo-degradation. A great variety of stabilizers are known in the art for stabilizing a diversity of substrates. Their effectiveness varies depending upon the causes of degradation and the substrate stabilized. In general, it is difficult to predict which stabilizer will be most effective and most economical for any one area of application. For example stabilizer effectiveness in reducing volatility may depend upon preventing bond scission in the substrate molecule. Limiting embrittlement and retaining elasticity in a polymer or rubber may require prevention of excessive crosslinking and/or chain scission. Prevention of discoloration may require inhibiting reactions which yield new chromophores or color bodies in the substrate or stabilizer. Problems of process stability and incompatibility must also be considered.

It has now been determined that the 4-hydroxybenzylthio aldehydes and ketones of this invention possess an unusual combination of desirable properties which makes them particularly effective and useful as stabilizers. The compounds are particularly effective in protecting polyolefins, high impact polystyrene, rubbers such as polybutadiene and styrene-butadiene rubber, and other elastomers wherein retention of elasticity and inhibition of cross-linking, crazing, discoloration, odor formation and exudation are basic requirements.

It is the primary object of this invention to provide a class of hydroxybenzylthio aldehydes and ketones which exhibit a broad range of improved stabilization performance characteristics.

Various other objects and advantages of this invention will become evident from the following description thereof.

The compounds of this invention correspond to the formula

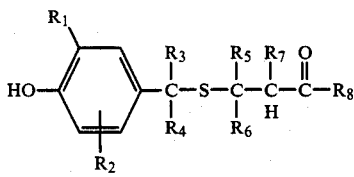

wherein $R_1-R_8$ independently are hydrogen, alkyl of 1 to 12 carbon atoms, cycloalkyl of 5 to 6 carbon atoms, phenyl, phenyl substituted by alkyl of 1 to 12 carbon atoms, aralkyl of 7 to 9 carbon atoms or said aralkyl substituted by alkyl of 1 to 12 carbon atoms.

Preferred compounds within the above structure are those wherein both $R_1$ and $R_2$ are in the ortho position to the hydroxy group.

As $C_1-C_{12}$ alkyl, the R groups are staight-chain or branched alkyl, preferably with 1 to 8 carbon atoms, such as methyl, n-butyl, sec-butyl, tert-butyl, tert-pentyl, hexyl, 2-ethylhexyl, n-octyl and 1,1,3,3-tetramethylbutyl. Methyl and tert-butyl are particularly preferred.

When the R groups are aralkyl they represent benzyl, α-methylbenzyl or α,α-dimethylbenzyl. Substituted phenyl can be for example tolyl, mesityl or xylyl.

The preferred embodiments have $R_1$ as tert.butyl, $R_2$ as methyl or tert.butyl, $R_3$ as hydrogen or methyl, $R_4$ as hydrogen, methyl or isopropyl and $R_5-R_8$ independently as hydrogen or methyl.

The stabilizer compounds are prepared by reacting a mercaptan of formula 1 with the unsaturated carbonyl compound of formula 2 in the presence of a catalyst

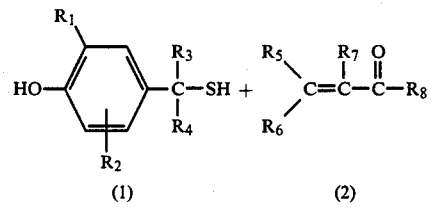

wherein $R_1-R_8$ are as previously defined.

The catalyst can be trialkyl amines such as triethyl amine, pyridine, sodium or potassium hydroxide, sodium or potassium carbonate, and the like. The synthesis can, if desired, be conducted in the presence of various solvent types such as alcohols, hydrocarbons, ethers, chlorinated hydrocarbons, aromatics, and the like. The reaction temperature generally ranges from $-10°$ C. to $150°$ C. with a preferred range of about $20°$ to $125°$ C. The starting materials are items of commerce or can be prepared by known methods.

Compounds of this invention are particularly effective in stabilizing organic materials such as plastics, polymers and resins in addition to mineral and synthetic fluids such as lubricating oils, circulating oils, etc.

Substrates in which the compounds of this invention are particularly useful are polyolefins such as polyethylene and polypropylene; polystyrene, including especially impact polystyrene; ABS resin; elastomers such as e.g. butadiene rubber, EPM, EPDM, SBR and nitrile rubber.

In general polymers which can be stabilized include

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under 1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrine homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under, (8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane]terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methylcellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellithates) and also mixtures of synthetic esters with mineral oils in any weight ratios, which materials may be used as plasticizer for polymers or as textile spinning oils, as well as aqueous emulsions of such materials.

29. Aqueous emulsions of natural or synthetic rubber, e.g. natural latex or latices of carboxylated styrene/butadiene copolymers.

In general, the stabilizers of this invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain various conventional additives, such as the following.

1. Antioxidants 1.1. Alkylated monophenols, for example,
2,6-di-tert.butyl-4-methylphenol
2-tert.butyl-4,6-dimethylphenol
2,6-di-tert.butyl-4-ethylphenol
2,6-di-tert.butyl-4-n-butylphenol
2,6-di-tert.butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert.butyl-4-methoxymethylphenol 1.2. Alkylated hydroquinones, for example,
2,6-di-tert.butyl-4-methoxyphenol
2,5-di-tert.butyl-hydroquinone
2,5-di-tert.amyl-hydroquinone
2,6-diphenyl-4-octadecyloxyphenol 1.3. Hydroxylated thiodiphenyl ethers, for example
2,2'-thio-bis-(6-tert.butyl-4-methylphenol)
2,2'-thio-bis-(4-octylphenol)
4,4'-thio-bis-(6-tert.butyl-3-methylphenol)
4,4'-thio-bis-(6-tert.butyl-2-methylphenol)

1.4. Alkyliden-bisphenols, for example,
2,2'-methylene-bis-(6-tert.butyl-4-methylphenol)
2,2'-methylene-bis-(6-tert.butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert.butylphenol)
2,2'-ethylidene-bis-(4,6-di-tert.butylphenol)
2,2'-ethylidene-bis-(6-tert.butyl-4-isobutylphenol)
4,4'-methylene-bis-(2,6-di-tert.butylphenol)
4,4'-methylene-bis-(6-tert.butyl-2-methylphenol)
1,1-bis-(5-tert.butyl-4-hydroxy-2-methylpheny)-butane
2,6-di-(3-tert.butyl-5-methyl-2-hydroxybenzyl)-4- methylphenol
1,1,3-tris-(5-tert.butyl-4-hydroxy-2-methylphenyl)-butane
1,1-bis-(5-tert.butyl-4-hydroxy-2-methylphenyl)-3-n-dodecylmercaptobutane
ethylenglycol-bis-[3,3-bis-(3'-tert.butyl phenyl)-butyrate]
di-(3-tert.butyl-4-hydroxy-5-methylphenyl)-dicyclopentadiene
di-[2-(3'-tert.butyl-2'-hydroxy-5'-methyl-benzyl)-6-tert.butyl-4-methylphenyl]-terephthalate.

1.5. Benzyl compounds, for example,
1,3,5-tri-(3,5-di-tert.butyl-4-hydroxybenzyl)-2,4,6-trimethylbenzene-di-(3,5-di-tert.butyl- 4-hydroxybenzyl)sulfide
3,5-di-tert.butyl-4-hydroxybenzyl-mercapto-acetic acid isooctyl ester
bis-(4-tert.butyl-3-hydroxy-2,6-dimethylbenzyl)dithiolterephthalate
1,3,5-tris-(3,5-di-tert.butyl-4-hydroxybenzyl)-isocyanurate
1,3,5-tris-(4-tert.butyl-3-hydroxy-2,6-dimethylbenzyl)isocyanurate
3,5-di-tert.butyl-4-hydroxybenzyl-phosphoric acid-dioctadecyl ester
3,5-di-tert.butyl-4-hydroxybenzyl-phosphoric acid-monoethyl ester, calcium-salt 1.6. Acylaminophenols, for example,
4-hydroxy-lauric acid anilide
4-hydroxy-stearic acid anilide
2,4-bis-octylmercapto-6-(3,5-tert.butyl-4-hydroxyanilino)-s-triazine
octyl-N-(3,5-di-tert.butyl-4-hydroxyphenyl)-carbaminate 1.7. Esters of β-(3,5-di-tert.butyl-4-hydroxyphenyl)propionic acid with monohydric or polyhydric alcohols, for example,

| | |
|---|---|
| methanol | diethyleneglycol |
| octadecanol | triethyleneglycol |
| 1,6-hexanediol | pentaerythritol |
| neopentylglycol | tris-hydroxyethyl isocyanurate |
| thiodiethyleneglycol | di-hydroxyethyl oxalic acid diamide |

1.8. Ester of β-(5-tert.butyl-4-hydroxy-3-methylphenyl)propionic acid with monohydric or polyhydric alcohols, for example,

| | |
|---|---|
| methanol | diethyleneglycol |
| octadecanol | triethyleneglycol |
| 1,6-hexanediol | pentaerythritol |
| neopentylglycol | tris-hydroxyethyl isocyanurate |
| thiodiethyleneglycol | di-hydroxyethyl oxalic acid diamide |

1.9. Amides of β-(3,5-di-tert.butyl-4-hydroxyphenyl)-propionic acid for example,
N,N'-di-(3,5-di-tert.butyl-4-hydroxyphenylpropionyl)-hexamethylendiamine
N,N'-di-(3,5-di-tert.butyl-4-hydroxyphenylpropionyl)-trimethylendiamine
N,N'-di-(3,5-di-tert.butyl-4-hydroxyphenylpropionyl)-hydrazine 2. UV absorbers and light stabilizers 2.1. 2-(2'-Hydroxyphenyl)-benztriazoles, for example, the 5'-methyl-, 3',5'-di-tert.butyl-, 5'-tert.butyl-, 5'-(1,1,3,3-tetramethylbutyl)-, 5-chloro-3',5'-di-tert.butyl-, 5-chloro-3'-tert.butyl-5'-methyl-, 3'-sec.butyl-5'-tert.butyl-, 4'-octoxy, 3',5'-di-tert.amyl-, 3',5'-bis-(β,β-dimethylbenzyl)-derivative.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivative.

2.3. Esters of optionally substituted benzoic acids for example, phenyl salicylate, 4-tert.butyl-phenylsalicylate, octylphenyl salicylate, dibenzoylresorcinol, bis-(4-tert.butylbenzoyl)-resorcinol, benzoylresorcinol, 3,5-di-tert.butyl-4-hydroxybenzoic acid 2,4-di-tert.butyl-phenyl ester and 3,5-di-tert.-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxycinnamic acid methyl ester, N-(β-carbomethoxy-β-cyanovinyl)-2-methyl-indoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-di-ethanolamine, nickel dibutyldithiocarbamate, nickel salts of 4-hydroxy-3,5-di-tert.butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazol, optionally with additional ligands.

2.6. Sterically hindered amines, for example bis-(2,2,6,6-tetramethylpiperidyl)-sebacate bis-(1,2,2,6,6-pentamethylpiperidyl)-sebacate n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylendiamine and 4-tert.octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butanetetracarbonic acid, 1,1'(1,2-ethanediyl)-bis-(3,3,5,5-tetramethyl-piperazinone).

2.7. Oxalic acid diamides, for example, 4,4'-dioctyloxyoxanilide, 2,2'-di-octyloxy-5,5'-di-tert.butyl-oxanilide, 2,2'-di-dodecyloxy-5,5'-di-tert.butyl-oxanilide, 2-ethoxy2'-ethyl-oxanilide, N,N'-bis (3-dimethylaminopropyl)oxalamide, 2-ethoxy-5-tert.butyl-2'-ethyloxanilide and its mixture with 2-ethoxy-2'-ethyl-5,4'-di-tert.butyloxanilide and mixtures of ortho- and para-methoxy-as well as of oand p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert.butyl-4-hydroxyphenylpropionyl)-hydrazine, 3-salicyloylamino1,2,4-triazole, bis-benzyliden-oxalic acid dihydrazide.

4. Phosphites and phosphonites, for example, triphenyl phosphite, diphenylalkyl phosphites, phenyldialkyl phosphites, tri-(nonylphenyl)phosphite, trilauryl phosphite, trioctadecyl phosphite, di-stearyl-pentaerythritol diphosphite, tris-(2,4-di-tert.butylphenyl) phosphite, di-isodecylpentaerythritol diphosphite, di-(2,4-di-tert.butylphenyl)pentaerythritol diphosphite, tristearyl-sorbite triphosphite, tetrakis-(2,4-di-tert.butylphenyl)-4,4'-diphenylylendiphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc-dibutyl-dithiocarbamate, dioctadecyldisulfide, pentaerythritol-tetrakis-(β-dodecylmercapto)-propionate.

6. Polyamide stabilizers, for example copper salts in combination with iodides and/or phosphorus compounds and salts of divalent manganese.

7. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for eample, 4-tert.butyl-benzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxydes, carbon black, graphite.

10. Other additives, for example, plasticizers, lubricants, emulsifiers, pigments, optical brighteners, flameproofing agents, anti-static agents, blowing agents and thiosynergists such as dilaurylthiodipropionate or distearylthiodipropionate.

The following examples illustrate the embodiments of this invention. In these examples, all parts given are by weight unless otherwise specified.

EXAMPLE 1

3-(3,5-di-t.butyl-4-hydroxybenzylthio)butyraldehyde 0.5 ml of triethylamine was added to a solution of 25.2 grams (0.10 mole) of 3,5-di-tert-butyl-4-hydroxybenzyl mercaptan, 7.0 grams (0.10 mole) of crotonaldehyde in 20 ml methanol, while stirring at room temperature. An exothermic reaction ensued which caused the temperature to rise to ca. 40° C. When the exotherm had subsided, the reaction mixture was heated at ca. 50° C. for three hours, then allowed to cool to room temperature. The methanol and triethylamine were stripped in vacuo and the resulting residue crystallized from hexane. This afforded 25.0 grams of white solids having M.P. 55°–60° C.

EXAMPLE 2

3-(3,5-di-t.butyl-4-hydroxybenzylthio)-3-phenylpropionaldehyde

A stirred solution of 12.6 grams (0.05 mole) of 3,5-di-tert-butyl-4-hydroxybenzyl mercaptan, 6.6 grams (0.05 mole) cinnamyl aldehyde and 25 ml hexane, was mixed with 0.5 ml triethylamine at room temperature. The reaction mixture was then heated at ca. 50° C. for six hours and then allowed to stand at ambient temperature overnight. The hexane and triethylamine were stripped under vacuum. A sample of the residue was purified chromatographically. 3.9 grams of light yellow solids were thus recovered, which had M.P. 75°–9° C.

EXAMPLE 3

3-(3,5-di-t.butyl-4-hydroxybenzylthio)propionaldehyde

A stirred solution consisting of 12.6 grams (0.05 mole) of 3,5-di-tert-butyl-4-hydroxybenzyl mercaptan, 2.8 grams (0.05 mole) of acrolein and 20 ml hexane was treated with 0.55 c.c. of triethylamine. Upon warming the mixture, an exothermic reaction ensued causing the temperature to rise to 55° C. The exotherm subsided within 10–15 min (to 35° C.). The reaction mixture was heated to 60°–65° C. for three hours, then allowed to cool and to stand at room temperature overnight. The hexane and triethylamine were stripped under vacuum and a sample of the residue was purified chromatographically. 2.9 grams of a light yellow syrup resulted.

EXAMPLE 4

3-(3-methyl-5-t. butyl-4-hydroxybenzylthio) butyraldehyde

A stirred solution of 21.03 grams (0.10 mole) of 3-methyl-5-tert-butyl-4-hydroxybenzyl mercaptan in 25 ml of tetrahydrofuran was mixed at room temperature dropwise over 15 minutes with a solution of 0.2 grams (0.002 mole) of triethylamine in 10.5 grams (0.15 mole) of crotonaldehyde. A mild exotherm (to 38° C.) occurred. After the exotherm subsided, the reaction mixture was heated at 50° C. for a total of four hours. Thin layer chromatography analysis at this point indicated complete reaction. After cooling to room temperature (overnight), the mixture was treated with 150 ml of ether and washed successively with water and saturated sodium chloride solution. The ether layer was dried over molecular sieves, then filtered and stripped in vacuo on a rotofilm evaporator. The resulting residue, a light yellow syrup, weighed 23.9 grams and consisted of substantially pure product (TLC, elemental evidence).

EXAMPLE 5

4-(3,5-di-t.butyl-4-hydroxybenzylthio)-5-methyl-hexane-2one 0.5 grams of triethylamine was added to a stirred solution consisting of 13.0 grams (0.051 mole) of 3,5-di-tert-butyl-4-hydroxybenzyl mercaptan, 7.2 grams (0.051 mole) of 5-methyl-3-hexene-2-one in 15 c.c. of hexane, with stirring at room temperature to ca. 31° C. After the exotherm had subsided (within ca. 15 minutes), the reaction mixture was heated to 40°–45° C. and maintained at this temperature for two days. After cooling to ambient temperatures, the mixture was stripped under vacuum. A sample of the resulting residue was purified chromatographically and an off-white syrup was isolated.

EXAMPLE 6

4-methyl-4-(3,5-di-t.butyl-4-hydroxybenzylthio)pentane-2-one

A stirred solution of 13.0 grams (0.051 mole) of 3,5-di-tert-butyl-4-hydroxybenzyl mercaptan, 5.0 grams (0.051 mole) of mesityl oxide in 20 c.c. of hexane, was mixed at room temperature with 0.5 grams of triethylamine. The reaction mixture was then heated to 50° C. for ca. 6 hours and then at ca. 75° C. for 1½ hours. It was then allowed to stand and cool overnight. The following day, several drops of piperidine were added and the reaction mixture heated four additional days at 75°–85° C. Finally, after cooling to room temperature, the reaction mixture was stripped under vacuum and an aliquot purified chromatographically. A sample of light yellow solids was thus obtained, which had M.P. 60°–68° C.

EXAMPLE 7

4-(3-methyl-5-t.butyl-4-hydroxybenzylthio)-5-methylhexane-2-one

A stirred solution consisting of 10.7 grams (0.051 mole) of 3-methyl-5-tert-butyl-4-hydroxybenzyl mercaptan, 7.2 grams (0.051 mole) of 5-methyl-3-hexene-2-one in 25 c.c. of hexane was treated at room temperature with 0.5 grams of triethylamine. The reaction mixture was then heated at 50°–55° C. for 7½ hours, then allowed to cool and stand at room temperature overnight. The following day all volatiles were removed under vacuum. A sample of the residue was chromatographed to yield a white semi-solid product which had M.P. 30°–32° C.

EXAMPLE 8

This example illustrates the stabilizing effectiveness of the instant stabilizers in impact polystyrene.

In the laboratory procedure utilized herein, a solution of eight weight percent polybutadiene rubber (Firestone—DIENE 55) dissolved in styrene monomer was prepared on a roller mill. The indicated amount of stabilizer was also introduced at this point. 500 ppm of zinc stearate was added to aid in removing the sample from the bottle after the polymerization. The bottle was screwed into the polymerization apparatus which was equipped with a double helical ribbon stirrer. Since most commercial IPS bulk polymerizations are thermally initiated processes, no initiator was used in the laboratory process. A nitrogen atmosphere was established and then the reactor was heated to 121° C. within ½ hours. Heating continued at 121° C. with efficient stirring until there was a 30 to 35% monomer conversion (2½ hours). The stirring rate was controlled to yield a two to four μm rubber particle size. The bottles were removed from the polymerization apparatus, blanketed with nitrogen, capped, and then placed in a fluidized bed sand bath to complete the polymerization. The bottles were heated in the bath in the following fashion: one hour at 100° C. to equilibrate the temperature, one hour to reach 140° C. and then an additional eight hours with the temperature increasing at the rate of 10° C. per hour to a maximum of 220° C. After the resin had cooled, the bottle was broken and the glass was removed. The average weight of the polymer block was slightly over 600 grams. The block was then placed into a vacuum oven at 200° C. and a vacuum of 1 mm applied as the polymer was heated for 45 minutes in order to remove all volatiles. The block was removed from the oven, immediately placed in a heated (205° C.) hydraulic press and then pressed into a thick slab between two sheets of aluminum foil (three minutes heating, five minutes in a cold press). The slab was split with a band saw and the pieces were granulated.

All batches were extruded at 205° C. and then pelletized. The pellets were compression molded at 205° C. into 125 mil tensile bars. The bars were then aged at 150° C. on glass plates placed on rotating shelves in a forced air oven. Other tensile bars were aged at 80° C. suspended from rotating shelves in a forced air oven. The specimen yellowness index was determined on the bars at various intervals according to ASTM D-1925-63T. Correspondingly, the bars were periodically measured for percent elongation in the Instron Tensile Testing Apparatus (Instron Engineering Corporation, Massachusetts) at a pull rate of 5 mm/minute according to ASTM D638.

| | Oven Aged Samples at 80° C. | | | | | |
|---|---|---|---|---|---|---|
| Additive | Conc. (% by wt.) | 0 Hrs. | 300 Hrs. | 600 Hrs. | 900 Hrs. | 1200 Hrs. |
| | | % Elongation | | | | |
| None* | — | — | — | — | — | 4 |
| Compound of Example 4 | 0.10 | 33 | 20 | 11.6 | 9.3 | 11.2 |
| Compound of Example 5 | 0.10 | 58 | 35 | 24.2 | 19.8 | 13.7 |
| Compound of Example 6 | 0.10 | 35 | 21 | 14.1 | 11.1 | 9.4 |
| Compound of Example 7 | 0.10 | 44 | 30 | 22 | 20.5 | 16.7 |
| | | Yellowness Index | | | | |
| None* | — | −12 | — | — | — | 47 |
| Compound of Example 4 | 0.10 | −9 | 4 | 11 | 18 | 20 |
| Compound of Example 5 | 0.10 | −10 | −2 | 10 | 20 | 28 |
| Compound of Example 6 | 0.10 | −5 | −8 | 10 | 16 | 19 |
| Compound of Example 7 | 0.10 | −7 | −0.6 | 6 | 10 | 12 |

| | Oven Aged Samples at 150° C. | | | | | |
|---|---|---|---|---|---|---|
| Additive | Conc. (% by wt.) | 0 Min. | 30 Min. | 60 Min. | 90 Min. | 120 Min. |
| | | % Elongation | | | | |
| None* | — | — | — | 12 | — | 6 |
| Compound of Example 1 | 0.10 | 32 | 30 | 32 | 17 | 14 |
| Compound of Example 4 | 0.10 | 33 | 29 | 24 | 19 | 11 |

| | -continued | | | | |
|---|---|---|---|---|---|
| Compound of Example 5 | 0.10 | 58 | 48 | 35 | 30 | 21 |
| Compound of Example 6 | 0.10 | 35 | 31 | 25 | 19 | 14 |
| Compound of Example 7 | 0.10 | 44 | 33 | 29 | 24 | 22 |
| | | Yellowness Index | | | | |
| None* | — | −12 | — | −7 | — | 1 |
| Compound of Example 1 | 0.10 | −13 | −9 | −10 | −4 | −3 |
| Compound of Example 4 | 0.10 | −9 | −6 | −7 | −4 | −2 |
| Compound of Example 5 | 0.10 | −10 | −9 | −7 | −7 | −2 |
| Compound of Example 6 | 0.10 | −5 | −3 | −1 | 3 | 5 |
| Compound of Example 7 | 0.10 | −7 | −5 | −3 | −2 | −1 |

*contains 0.025% by weight, of octadecyl 3-(3',5'-di-t.-butyl-4-hydroxyphenyl)propionate as processing aid This Example thus indicates the effective stabilizing performance of the instant compounds.

Summarizing, it is seen that this invention provides a group of compounds which have excellent stabilizing activity in a variety of organic materials. Variations may be made in proportions, procedures and materials without departing from the scope of the invention as defined by the following claims.

What is claimed is:

1. A compound of the formula

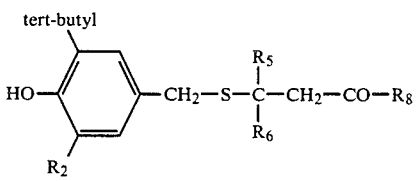

Wherein
$R_2$ is methyl or tert-butyl,
$R_5$ is hydrogen or methyl,
$R_6$ is hydrogen, alkyl of 1 to 3 carbon atoms or phenyl, and
$R_8$ is hydrogen or methyl.

2. A compound according to claim 1 wherein $R_8$ is hydrogen.

3. 3-(3,5-di-tert-butyl-4-hydroxybenzylthio)-butyraldehyde according to claim 1.

4. 3-(3,5-di-tert-butyl-4-hydroxybenzylthio)-3-phenylpropionaldehyde according to claim 1.

5. 3-(3,5-di-tert-butyl-4-hydroxybenzylthio)propionaldehyde according to claim 1.

6. 3-(3-methyl-5-tert-butyl-4-hydroxylbenzylthio)-butyraldehyde according to claim 1.

7. 4-(3,5-di-tert-butyl-4-hydroxybenzylthio)-5-methyl-hexane-2-one according to claim 1.

8. 4-methyl-4-(3,5-di-tert-butyl-4-hydroxybenzylthio)pentane-2-one according to claim 1.

9. 4-(3-methyl-5-tert-butyl-4-hydroxybenzylthio)-5-methyl-hexane-2-one according to claim 1.

10. A composition of matter comprising a lubricating oil subject to oxidative, thermal and actinic degradation stabilized with an effective stabilizing amount of a compound of claim 1.

* * * * *